United States Patent [19]

Linder

[11] 4,369,991

[45] Jan. 25, 1983

[54] CONNECTOR FOR ENDOTRACHEAL TUBES AND CATHETERS

[76] Inventor: Gerald S. Linder, 16693 Charmel La., Pacific Palisades, Calif. 90272

[21] Appl. No.: 81,694

[22] Filed: Oct. 4, 1979

[51] Int. Cl.³ ............................................. F16L 35/00
[52] U.S. Cl. ..................................... 285/38; 128/247; 285/177; 285/272; 285/423; 285/179
[58] Field of Search ................ 285/38, 260, 272, 177, 285/238, 239, 423, 275, 179; 128/203.11-203.29, 207.14, 247

[56] References Cited

U.S. PATENT DOCUMENTS

| | | | |
|---|---|---|---|
| 195,311 | 9/1877 | Sterling | 285/38 |
| 1,910,706 | 5/1933 | Malzard | 285/38 X |
| 2,577,045 | 12/1951 | Stout | 128/203.21 X |
| 2,641,253 | 6/1953 | Engelder | 128/203.21 X |
| 3,129,020 | 4/1964 | Bujnowski | 285/260 X |
| 3,552,778 | 1/1971 | Muller | 285/260 X |
| 3,912,795 | 10/1975 | Jackson | 128/203.12 X |
| 3,938,834 | 2/1976 | Oostenbrink | 285/423 X |
| 3,997,195 | 12/1976 | Bartholomew | 285/423 X |
| 4,152,017 | 5/1979 | Abramson | 285/260 X |

FOREIGN PATENT DOCUMENTS

| | | | |
|---|---|---|---|
| 705031 | 3/1965 | Canada | 285/238 |
| 825564 | 10/1969 | Canada | 285/260 |
| 1230358 | 3/1960 | France | 285/177 |
| 928911 | 6/1963 | United Kingdom | 285/260 |
| 1246490 | 9/1971 | United Kingdom | 285/238 |

Primary Examiner—Dave W. Arola
Attorney, Agent, or Firm—B. F. Spencer

[57] ABSTRACT

An improved connector is disclosed for coupling the output breathing circuit connection from a conventional anesthesiology machine to the open proximal end of a conventional endotracheal tube. The connector includes a cylindrical input section, a central flange portion, a cylindrical output section, and a bore extending concentrically therethrough. The input section is provided with a stepped outer cylindrical surface for coupling to the breathing circuit connection. The flange portion is provided with sides or faces to facilitate manual gripping of the connector between the thumb and fingers. Openings are provided through a part of the flange portion to permit the connector to be physically tied to the breathing circuit connection. The inner cylindrical wall of the bore of the cylindrical output section is provided with a narrow ridge or annular ring projecting radially inward. The connector is installed upon the endotracheal tube by rotatably sliding the cylindrical output section over the outer cylindrical surface of the open proximal end of the endotracheal tube. The narrow ridge or annular ring presses into the outer surface of the endotracheal tube to form an airtight seal between the connector and the endotracheal tube. The connector is rotatable in its installed position upon the endotracheal tube in a swivel-like manner without physical movement of the endotracheal tube and without loss of the airtight seal.

15 Claims, 6 Drawing Figures

TO ANESTHESIOLOGY MACHINE

TO ANESTHESIOLOGY MACHINE

CONNECTOR FOR ENDOTRACHEAL TUBES AND CATHETERS

BACKGROUND OF THE INVENTION

The present invention relates to connectors for use with endotracheal tubes and catheters.

Connectors are used for coupling the breathing circuit connection from the output of conventional anesthesiology machines to the open proximal end of the endotracheal tube. The conventional connector generally is molded of relatively hard plastic or polymer material and consists of a hollow cylindrical body having a cylindrical input section, a cylindrical output section or spout, and a central portion to facilitate holding the connector between the thumb and fingers. The cylindrical input section is of standard and uniform size to receive over its outer surface the standard breathing circuit connection or elbow connector which is attached to the output of the flexible hose from the anesthesiology machine. The outer surface of the cylindrical input section usually is tapered, or slightly conical, to insure an airtight seal between the outer surface and the inner cylindrical surface of the breathing circuit connection. The airtight seal is achieved by firmly pressing the two mating surfaces together.

The cylindrical output section, or spout, of the conventional connector is of widely varying sizes to accommodate the different sizes of endotracheal tubes in use. The spout is tapered and is inserted into the open proximal end of the endotracheal tube of the proper mating size to achieve a tight press fit, thereby assuring an airtight seal between the spout and the endotracheal tube.

Modern endotracheal tubes and catheters are manufactured of polyvinyl chloride, a tough, though flexible, transparent or semi-transparent rubber-like material. This material is well suited for this use since its surface texture and pliability are readily controllable during manufacture. The material, however, does possess two characteristics which have presented some problems in its use for endotracheal tubes. The first is that the material tends to age with the passage of time as well as when exposed to certain atmospheric conditions, resulting in a loss of flexibility and clarity in color. The second is that when the material is subjected to stress forces, as by bending or expanding, a temporary or semi-permanent set occurs within the material. Upon removal of the stress-producing forces, this set will gradually dissipate, and the material will return slowly to its original shape.

This latter characteristic produces a problem when an endotracheal tube of polyvinyl chloride is used with the tapered spout of the conventional hard plastic connector. While a secure and tight-fitting coupling is achieved between the outer conical surface of the spout and the inner cylindrical surface of the proximal end of the endotracheal tube when the spout is first inserted into the endotracheal tube, this tight fit begins to diminish almost immediately as the forces produced in expanding the diameter of the endotracheal tube cause the polyvinyl chloride to lose its resiliency and to take on a semi-permanent set. In those cases where an operation upon a patient may consume a period of many minutes, not to mention hours, it has been found that the fit between the spout and the proximal end of the endotracheal tube has become loose. It is not uncommon, under these circumstances, for the connector to become completely detached from the endotracheal tube, thereby causing an immediate loss of anesthesia.

The problem is not as acute where the conventional hard plastic connector is used with catheters which are intended for intubation into the mucous canals of the patient for the purpose of drainage of viscous fluids. In this type of operation, the physician may, after intubation of the catheter, desire to remove the connector from the proximal end of the catheter. The hard plastic connector, with its smooth tapered spout, is more easily removed from the proximal end of a polyvinyl chloride catheter after the proximal end has expanded in diameter and the set has begun to take effect.

Connectors have been fabricated from a variety of different materials, other than hard plastic, including materials having a relatively pliable and resilient characteristic similar to that of natural rubber. While tight-fitting seals have been achieved with these connectors, the removal of the connector from the catheter or endotracheal tube is virtually impossible. The forces needed to be applied by the physician to remove the connector from the endotracheal tube or catheter are found to be too great. Such forces cause actual physical movement of the intubated endotracheal tube or catheter and its resulting trauma to the patient. This problem becomes extremely acute in those cases requiring the physical removal of the connector from an intubated endotracheal tube or catheter during operations performed in emergency situations.

One type of connector, known as the "Racine" connector, consists of a long, corrugated, silicone rubber tube having a cylindrical metal input section for coupling to the breathing circuit connection. The output section consists of a stretched silicone rubber diaphragm supported perpendicularly across the output end of the corrugated tube by a metal ring. A small circular hole is located in the center of the diaphragm.

The stretched diaphragm, with its center hole, is adapted for stretching over the outside surface of the proximal end of the endotracheal tube by expanding the diameter of the central hole. A relatively tight seal is achieved over the outside surface of the endotracheal tube rather than within its cylindrical inside surface. The "Racine" connector is usable with a number of sizes of endotracheal tubes without altering the diameter of the center hole in the stretchable diaphragm. While this type connector possesses some advantages over the conventional hard plastic connector, its cost is relatively high.

A number of additional serious problems exist with the use of the conventional connector. These problems, however, have been substantially eliminated by the introduction of the improved connector of the invention.

Accordingly, a principal object of the present invention is to provide an improved connector of a new type capable of providing a superior seal between connector and endotracheal tube.

Another important object is to provide a connector that may be installed easily upon an endotracheal tube or catheter and thereafter may be removed from the endotracheal tube without disturbance of the position of the endotracheal tube or catheter.

A further object is to provide a connector for coupling to the endotracheal tube which does not restrict or reduce the size of the lumen of the endotracheal tube.

An additional object is to provide a new type of connector for use with endotracheal tubes or catheters, which is rotatable with respect to the endotracheal tube or catheter without loss of the airtight seal and without disturbance of the position of the endotracheal tube.

Still another object of the invention is to provide a connector whose bore is appreciably larger than the lumen of the endotracheal tube for which it is designed to be used, thereby enabling larger suction catheters to be inserted into and through the connector and endotracheal tube in those operations in which a suction catheter may be required.

Further objects include providing an improved connector capable of producing a longer-lasting airtight seal with the conventional endotracheal tube, a superior coupling between connector and breathing circuit connection, and an improved means for securing the connector to the breathing circuit of the anesthesiology machine.

SUMMARY OF THE INVENTION

The objects of the invention are achieved by providing a connector comprising a cylindrical input section, a cylindrical output section, a central flange portion, and a bore extending concentrically therethrough. The cylindrical input section is provided with a stepped outer cylindrical surface rather than a conically-tapered surface to assure a superior coupling to the breathing circuit connection.

The cylindrical output section is designed to slide over the outer surface of the proximal end of the conventional endotracheal tube. An internal annular ring or ridge, having a generally triangular cross section, is located within the cylindrical output section. The triangular-shaped annular ridge projects radially inward from the inner wall of the cylindrical output section by an amount approximating the thickness of the wall of the endotracheal tube. The tip of the triangular ridge is smooth and slightly rounded for pressing firmly into the outer surface of the tough, though resilient, endotracheal tube. By forming the improved connector of relatively hard plastic or polymer material, such as polypropylene, nylon, or the like, having a relatively low coefficient of friction, the rounded tip of the triangular-shaped ridge provides a bearing-like surface pressing into the outer surface of the endotracheal tube. The force upon the outer surface of the endotracheal tube, produced by the annular ridge, compresses the walls of the tube causing a continuous, circular depression or groove. An airtight seal is achieved between connector and endotracheal tube.

The bearing-like surface between the annular ridge and the continuous, circular depression in the surface of the endotracheal tube allows the connector to be rotated relative to and about the axis of the endotracheal tube in a swivel-like manner. Since the rounded tip of the annular, triangular-shaped ridge remains in physical contact with the circular depression or groove in the outer surface of the endotracheal tube, the airtight seal is retained during rotation of the connector. By selecting the inner diameter of the cylindrical output section to be slightly larger than the outer diameter of the endotracheal tube for which the connector is designed, any frictional contact between these two cylindrical surfaces is substantially reduced, thus assuring easy rotation of the connector relative to the endotracheal tube.

The central flange portion, located between the cylindrical input and output sections, is provided with suitable sides or faces to facilitate gripping the connector in order that the output section may be rotatably installed over the outer surface of the endotracheal tube. A group of openings or notches is provided through the central flange portion to enable the connector to be securely tied to the breathing circuit connection by bands or cords, should this become necessary or desirable.

An alternative embodiment of the invention places the annular ring or ridge upon the outer surface of the cylindrical output section with the tip of the triangular-shaped ridge projecting radially outward. In this embodiment, the outer diameter of the cylindrical output section should be slightly smaller than the inner diameter of the endotracheal tube for which the connector is designed. The cylindrical output section is inserted into the open proximal end of the endotracheal tube, and the annular ridge produces a force, causing a continuous, circular expansion in the inner wall of the endotracheal tube. An airtight seal is maintained between the annular ridge of the connector and the expanded, circular groove in the wall of the endotracheal tube. The connector is readily rotatable about the axis of the endotracheal tube in a swivel-like manner.

DESCRIPTION OF THE INVENTION

Figure 1:
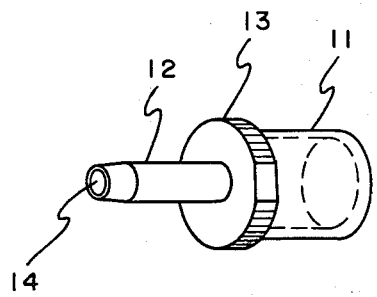
FIG. 1 is a perspective view of a type of prior art connector widely used with catheters and endotracheal tubes.

FIG. 1 illustrates a type of prior art connector composed of hard plastic material and consisting of a hollow cylindrical input section 11, a tapered output section or spout 12, a central portion 13, and an opening or bore 14 extending concentrically therethrough. The outer cylindrical surface of input section 11 is slightly tapered to provide a tight, mating fit with the inner diameter of the conventional breathing circuit connection. The spout 12 is manually inserted into the open proximal end of an endotracheal tube by the physician prior to intubation of the endotracheal tube. The connector of FIG. 1 is readily usable with either endotracheal tubes or catheters.

Figure 2:
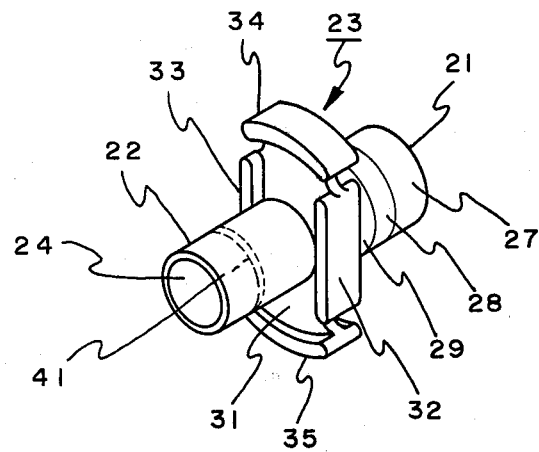
FIG. 2 is a perspective view of the preferred embodiment of the improved connector of this invention.
Figures 3, 4, 5:
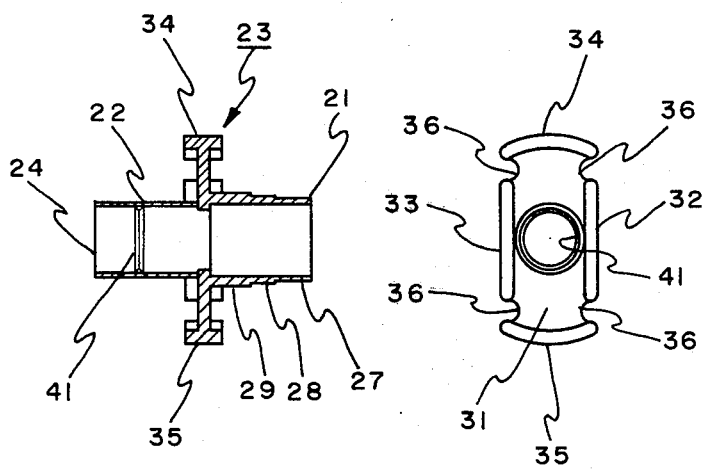
FIG. 3 is a side sectional view of the improved connector of FIG. 2.
FIG. 4 is a view of the connector of FIG. 2 taken from the output end.
FIG. 5 is a perspective view of an alternative embodiment of the invention.

The preferred embodiment of the invention is illustrated in perspective in FIG. 2, in cross section in FIG. 3, and as viewed from the output end in FIG. 4. The connector comprises a hollow cylindrical input section 21, a hollow cylindrical output section 22, a central flange portion 23, and a bore 24 extending therethrough. The outer cylindrical surface of input section 21 may be slightly tapered, as in the prior art, or it may consist of three slightly reduced diameter portions in steps, as illustrated in FIGS. 2 and 3. The diameter of cylindrical portion 27 adjacent the input opening is slightly smaller than the diameter of cylindrical portion 28, which in turn is slightly smaller than the diameter of cylindrical portion 29. An improved fit between connector and breathing circuit connection is achieved with this design over that of the conventional tapered input section.

Central flange portion 23 includes a thin central web 31 lying in a plane perpendicular to the axis of the connector. Web 31 supports two parallel side portions 32 and 33 and semicircular top and bottom portions 34 and 35. Four identical notches or openings 36 within web 31 are located between the side portions 32,33 and the top and bottom portions 34 and 35. The two side portions 32,33 provide convenient surfaces for manually holding the connector between the thumb and fingers. The four notches 36, with the arched top and bottom portions 34 and 35, provide suitable attachment positions for physically tying bands or cords between the connector and the breathing circuit connection, should this procedure become necessary during the operation of the recovery period.

The cylindrical output section 22 is provided with an internal annular ring or ridge 41 of triangular cross section projecting radially inward from the inside wall of the section. Annular ridge 41 is laterally positioned approximately half way between the open output end of section 22 and the center of flange portion 23, as illustrated in FIG. 3. Ridge 41 extends into the central bore by an amount approximately equal to the wall thickness of the endotracheal tube or catheter for which the connector is designed to be used. The tip of triangular-shaped ridge 41 is slightly rounded to prevent the tip from cutting into the outer cylindrical surface of the endotracheal tube.

The improved connector of FIGS. 2-4 may be molded from any suitable medically approved plastic or polymer material, such as nylon or polypropylene. A material possessing a relatively low surface coefficient of friction is preferred. While the cylindrical input section 21, with its stepped diameter portions 27, 28 and 29 are of standard size to fit the 15 millimeter breathing circuit connection, the cylindrical output section 22 will vary in size to accommodate the wide range of available sizes of endotracheal tubes and catheters. Endotracheal tubes vary from 2 millimeters for pediatric sizes up to 10 millimeters for large adults.

The outer cylindrical surface of output section 22 is shown as being of uniform diameter in FIGS. 2, 3 and 4 for ease of illustration. While output section 22 of the preferred embodiment is intended to be installed over the outer cylindrical surface of the proximal end of the endotracheal tube, it is apparent that the outer cylindrical surface may, if desired, be slightly tapered or even stepped to permit output section 22 to be used with the largest of the endotracheal tube sizes in the conventional manner.

FIG. 5 illustrates an alternative embodiment of the invention in which the connector comprises a hollow cylindrical input section 21 as in FIGS. 2-4, a hollow cylindrical output section 52, a central flange portion 53, and a bore 54 extending concentrically therethrough. Input section 21 is provided with three different outer diameter portions 27, 28 and 29, as in the preferred embodiment, to provide an improved coupling between the connector and the breathing circuit connection.

Central flange portion 53 is provided with side portions 55 for gripping the connector, and with upper and lower oval-shaped openings 56 and 57, extending through flange 53, to facilitate tying the connector to the breathing circuit connection.

Cylindrical output section 52 differs from that of the preferred embodiment by providing an external annular ring or ridge 61 projecting radially outward from the outer surface. Ridge 61 is positioned laterally between the open end of section 52 and the end surface of central flange 53. Ridge 61 may be of triangular cross section and extends radially outward by an amount approximately equal to the thickness of the endotracheal tube for which it is designed to be used. The tip of ridge 61 is slightly rounded. The connector may be molded from nylon or polypropylene, both of which possess a relatively low coefficient of friction.

Figure 6:
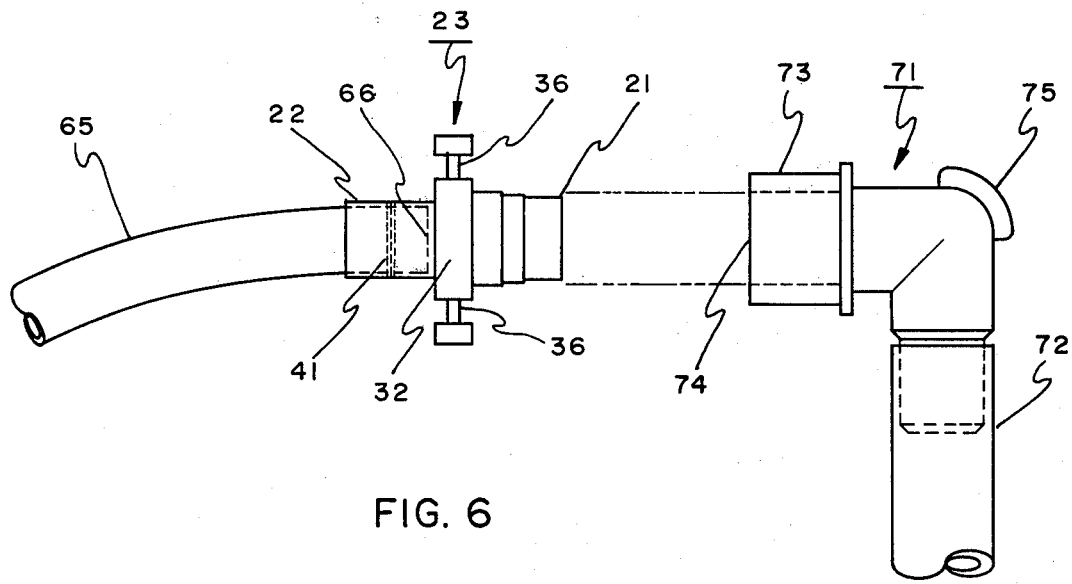
FIG. 6 illustrates the improved connector of FIG. 2 installed in position upon the outer cylindrical surface of the open proximal end of a conventional endotracheal tube.

FIG. 6 illustrates the manner in which the preferred embodiment of the connector of FIGS. 2-4 is installed upon the outer cylindrical surface of the open proximal end portion of endotracheal tube 65. A connector is selected whose output section 22 has an internal diameter somewhat larger than the outer diameter of the proximal end portion of tube 65. The proximal end portion is slideably inserted into bore 24 of output section 22 until the proximal end 66 reaches the internal annular ridge 41. The rounded tip of triangular-shaped ridge 41 is forced up and over proximal end 66 and upon the outer cylindrical surface of tube 65 by rotation of the connector about its axis while a thrust force is applied in the direction of endotracheal tube 65. The rotational and thrust forces upon the connector are maintained as annular ridge 41 slides over the outer surface until proximal end 66 abuts a stop within bore 24 adjacent to or within the central flange portion 23. The rotational thrust forces required to install the connector upon endotracheal tube 65 are readily produced by gripping sides 32, 33 between the thumb and fingers.

The force produced by the rounded tip of annular ridge 41 upon and into the outer surface of endotracheal tube 65 compresses the outer wall, causing a continuous, circular depression or groove to be formed into the outer wall surface. The compliance of the material from which the endotracheal tube is made enables the circular depression or groove in the outer wall surface to conform to the shape of the annular ridge 41 and its rounded tip. Since the forces producing the circular depression or groove are forces tending to compress the endotracheal tube, the resilience of the tube tends to oppose and resist the compression of the tube. Therefore, the rounded tip of ridge 41 remains in physical contact with the outer wall surface and within the circular groove to provide a long-lasting airtight seal.

A bearing-like surface is achieved between the rounded tip of annular ridge 41 and the outer surface of endotracheal tube 65 by molding the improved connector from a material having a low coefficient of friction. This characteristic enables the connector, with its internal annular ridge 41, to be easily installed upon the endotracheal tube, as shown in FIG. 6, and to be readily removed therefrom.

Since the internal diameter of output section 22 of the connector is slightly larger than the outer diameter of the proximal end portion of tube 65, little or no frictional contact or rubbing occurs between the inner cylindrical wall surface of output section 22 and the outer cylindrical surface of endotracheal tube 65. As a result, the bearing-like surface existing between the rounded tip of annular ridge 41 and the circular groove formed into the outer surface of endotracheal tube 65 permits the connector to be freely and easily rotated about its axis and the axis of tube 65 in its installed position without disturbance of endotracheal tube 65 and without loss of the airtight seal. This feature is of considerable interest to the physician as it allows the connector to be rotated relative to the endotracheal tube in a swivel-like manner either before or after the endotracheal tube has been intubated in the patient.

The lumen, or opening into the endotracheal tube, is not reduced or restricted by the installation of the connector of the preferred embodiment of the invention. Since the connector fits over the outer cylindrical surface of the tube, the full breathing capacity of the tube is available. This feature is of considerable importance to the physician and patient, especially where small adult or pediatric size endotracheal tubes must be used.

The breathing capacity of an intubated endotracheal tube is also important in those cases in which it becomes necessary for the physician to insert a suction catheter into and through the intubated endotracheal tube to drain or withdraw fluids developing in the patient's breathing channels. With the improved connector of this invention, a suction catheter may be inserted through the connector and intubated endotracheal tube. The practice of removing the connector from the intubated endotracheal tube to obtain the full breathing capacity of the tube is no longer required.

After intubation of the endotracheal tube with its connector in place, the physician will attach the output breathing circuit connection from the anesthesiology machine to the cylindrical input section of the connector. The ninety-degree elbow 71 of FIG. 6 is one example of the several standard types available for this purpose. The cylindrical input section of elbow 71 is attached to the end of flexible hose 72 leading from the anesthesiology machine.

Elbow 71 usually is composed of a hard plastic or polymer material, such as polypropylene, and includes a cylindrical output section 73 having a straight, smooth bore 74 of standard size. The output section 73 is adapted to fit tightly over the cylindrical input section of the connector, as illustrated in FIG. 6.

Where the breathing circuit connection is composed of a relatively hard plastic material having little or no resilience, as elbow 71, a superior seal between breathing circuit connection and connector can be achieved by providing cylindrical input section 21 with a series of stepped outer diameter portions 27, 28 and 29, as disclosed above. The bore 74 of elbow 71, being smooth and untapered, is free to accommodate itself upon any one of the several stepped portions providing the most desirable fit. As each stepped diameter portion is of uniform diameter, a tight fit upon at least one of the stepped portions can be achieved.

During prolonged intubation, or during recovery, the physician may desire to secure the connector to the breathing circuit connection by tying. The standard elbow 71 is provided with a crown 75 below which bands or cords may be wrapped. These bands or cords may be readily attached to the improved connector of this invention by passing them around the notches or openings 36 below arched top portion 34 and above arched bottom portion 35 of the preferred embodiment of the invention, or through openings 56 and 57 of the alternative embodiment of FIG. 5. However, the improved coupling between the connector of this invention and the breathing circuit connection from the anesthesiology machine provided by the series of stepped outer diameter portions 27, 28 and 29 of cylindrical input section 21 is believed to reduce substantially any need for tying.

The alternative embodiment of the invention illustrated in FIG. 5 is installed in a manner somewhat similar to that of the preferred embodiment of the invention, with the exception that cylindrical output section 52 with annular ridge 61 is inserted into the open proximal end of the endotracheal tube. Before installation, a connector is chosen whose output section 52 has an outer diameter somewhat smaller than the inner diameter of the proximal end portion of the endotracheal tube. Output section 52 is slideably inserted into the open proximal end portion until the proximal end reaches the external annular ridge 61. The rounded tip of the triangular-shaped ridge 61 is forced into the open proximal end by rotation of the connector about its axis while a thrust force is applied in the direction of the endotracheal tube. The rotational and thrust forces upon the connector are maintained as annular ridge 61 moves into the open proximal end portion until the proximal end abuts the surface of central flange portion 53. The forces required to install the connector are easily produced by gripping the two sides 55 of the connector between the thumb and fingers.

The force produced by the rounded tip of annular ridge 61 upon the inner cylindrical wall surface of the endotracheal tube expands the inner wall causing a continuous, circular expanded groove to be formed. By virtue of the compliance of the endotracheal tube, the expanded circular groove will conform to the shape of annular ridge 61 with its rounded tip. The resilience of the endotracheal tube tends to oppose and resist the expansion of the tube. As a result, the rounded tip of ridge 61 remains in physical contact with the inner wall surface and within the expanded, circular groove to provide a long-lasting airtight seal.

Since the outer diameter of output section 52 is slightly smaller than the inner diameter of the proximal end portion of the endotracheal tube, little or no frictional contact or rubbing occurs between the outer cylindrical surface of section 52 and the cylindrical inner wall surface of the endotracheal tube. A bearing-like surface will exist, therefore, between the rounded tip of annular ridge 61 and the expanded, circular groove within the inner wall surface of the endotracheal tube. This bearing-like surface permits the connector of FIG. 5 to be freely and easily rotated about its axis and the axis of the endotracheal tube in its installed position without disturbance of the endotracheal tube and without loss of the airtight seal. The physician may rotate the connector of FIG. 5 relative to the endotracheal tube in the same swivel-like manner by which the connector of the preferred embodiment of FIGS. 2-4 may be rotated.

The cylindrical input section 21 of the connector of FIG. 2 with its stepped outer diameter portions 27, 28 and 29 is adapted for coupling to the standard breathing circuit connector in the same manner as described above in connection with the preferred embodiment. The oval-shaped openings 56 and 57 are provided to enable the connector to be physically tied to the breathing circuit connection, if desired, in the manner described above in connection with FIG. 6.

Since many changes can be made in the above-described apparatus and many different embodiments of this invention could be made without departing from the scope thereof, it is intended that all matter contained in the above description or shown in the accompanying drawing shall be interpreted as illustrative and not in a limiting sense.

What is claimed is:

1. An improved connector for inter-coupling between the output breathing circuit connection of an anesthesiology machine and the smooth outer wall surface of the open proximal end of a cylindrical, resilient endotracheal tube, comprising in combination:
   (a) a hollow cylindrical body of relatively rigid, non-perforated material having an open input end adapted for coupling to the breathing circuit connection of an anesthesiology machine, said hollow cylindrical body further having an open output end adapted for sliding over the smooth outer wall surface of the proximal end portion of a cylindrical endotracheal tube, the inner diameter of the open output end of said hollow cylindrical body being slightly larger than the outer diameter of the cylindrical, resilient endotracheal tube for which the connector is designed to be used; and
   (b) a single annular internal ridge formed integrally within said hollow cylindrical body near the output end, said annular ridge projecting radially inward from the inner wall surface of said hollow cylindrical body, the tip of said annular internal ridge being adapted for physically engaging the smooth outer wall surface of and forming a depression into and continuously around the smooth outer wall surface of the proximal end portion of the endotracheal tube upon the insertion of the proximal end portion into the open output end of said hollow cylindrical body, said annular internal ridge thereby providing an air-tight seal between the smooth outer wall surface of the endotracheal tube and the inner wall surface of said hollow cylindrical body by the engagement of the tip of said annular ridge with the smooth outer wall surface of said resilient endotracheal tube, said annular ridge further maintaining physical separation between the inner cylindrical wall surface of the open end of said hollow body and the smooth outer cylindrical wall surface of the endotracheal tube adjacent each side of said annular ridge to minimize contact between the cylindrical wall surfaces, said connector being rotatable with respect to the endotracheal tube about the axis of said hollow, cylindrical body in a swivel-like manner while maintaining said air-tight seal.

2. The improved connector as defined by claim 1 wherein said annular internal ridge projects radially inward by an amount approximately equal to the thickness of the wall of the endotracheal tube for which the connector is designed to be used.

3. The improved connector as defined by claim 1 wherein said rigid material is polypropylene.

4. The improved connector as defined by claim 1 further comprising a central flange portion integrally formed upon and situated between the open input and output ends of said hollow cylindrical body, said central flange portion extending radially outward from the outer wall surface of said hollow cylindrical body for providing a suitable surface for gripping and holding the connector.

5. The improved connector as defined by claim 4 wherein said central flange portion includes a thin central web section, the plane of said central web section being perpendicular to the axis of said hollow cylindrical body.

6. The improved connector as defined by claim 5 wherein said central flange portion is provided with a plurality of openings, each of said openings passing through a part of said thin central web section.

7. The improved connector as defined by claim 4 wherein said central flange portion, extending radially outward from the outer surface of said hollow body, includes at least a pair of diametrically opposed openings passing therethrough.

8. The improved connector as defined by claim 1 wherein the outer cylindrical surface of the open input end of said hollow cylindrical body consists of a series of cylindrical sections of slightly different diameters, the diameter of each cylindrical section of the series being uniform.

9. The improved connector as defined by claim 8 wherein the diameter of the cylindrical section nearest the open input end is the smallest of the series.

10. An improved connector for coupling the output breathing circuit connection from an anesthesiology machine to the smooth outer wall surface of the open proximal end of a cylindrical, resilient endotracheal tube, comprising in combination:
   (a) a body of relatively rigid material having a hollow input section, said input section being adapted for coupling to the breathing circuit connection of an anesthesiology machine;
   (b) said body further having a hollow output section, said output section being adapted for sliding over the smooth outer wall surface of the proximal end portion of a cylindrical endotracheal tube, the inner diameter of said hollow output section being slightly larger than the outer diameter of the cylindrical, resilient endotracheal tube for which the connector is designed to be used for providing an airspace therebetween;
   (c) a bore extending through said body between said hollow input and output sections; and
   (d) an annular internal ridge formed integrally within said hollow output section and projecting radially inward from the inner wall surface, the tip of said internal annular ridge being adapted for physically engaging the smooth outer wall surface of and forming a continuous depression into and completely around the outer wall surface of the proximal end portion of the endotracheal tube upon insertion of the proximal end portion into said hollow output section, at least the portion of said body surrounding said bore and said proximal end portion of said endotracheal tube being nonperforated, said annular internal ridge thereby forming an air-tight seal between the connector and the endotracheal tube by engagement of the tip of said annular ridge with the smooth outer wall surface of said resilient endotracheal tube, the tip of said annular ridge providing a bearing-like surface in engagement with the continuous depression into and completely around the smooth outer wall surface of the endotracheal tube to enable relative rotation of the connector about the endotracheal tube in a swivel-like manner while maintaining said airtight seal.

11. The improved connector as defined by claim 10 wherein said internal annular ridge, projecting radially inward from the inner wall surface, is of triangular cross section, and wherein said triangular-shaped ridge has a rounded tip.

12. The improved connector as defined by claim 11 wherein said body of rigid material is composed of a polymer material having a low coefficient of friction.

13. An improved connector for coupling the output breathing circuit connection from an anesthesiology machine to the open proximal end of a cylindrical, resilient endotracheal tube, comprising in combination:
   (a) a body of relatively rigid material having a hollow input section, said input section being adapted for coupling to the breathing circuit connection of an anesthesiology machine;
   (b) said body further having a cylindrical output section, said cylindrical output section being adapted for sliding into the inner cylindrical surface of the open proximal end portion of a cylindrical endotracheal tube, the outer diameter of said cylindrical output section being slightly smaller than the inner diameter of the open proximal end of the cylindrical, resilient endotracheal tube for which the connector is designed to be used thereby providing an air space therebetween;
   (c) a bore extending through said body between said hollow input and output sections; and
   (d) an annular external ridge integrally formed upon and projecting radially outward from the outer cylindrical surface of said cylindrical output section, said annular external ridge being adapted for physically engaging and forming a continuous, expanded groove into and completely around the inner cylindrical wall surface of the proximal end portion of the endotracheal tube upon insertion of said cylindrical output section into the open proximal end of the endotracheal tube, the portion of said body surrounding said bore and in overlapping engagement with said endotracheal tube being nonperforated, said annular external ridge thereby forming an airtight seal between the connector and the endotracheal tube by engagement of the tip of said annular external ridge with the inner cylindrical wall surface of said resilient endotracheal tube.

14. The swivel coupling between one end of a resilient, hollow cylindrical tube and a rigid, hollow connector, comprising in combination:
   (a) a hollow tube of resilient material having a cylindrical inner surface, a cylindrical outer surface, and an open end;
   (b) a connector of rigid, nonperforated material having an input section, a cylindrical output section, and a bore extending therethrough, the open end of said resilient, hollow cylindrical tube and the rigid cylindrical output section being loosely inter-coupled one within the other in telescoping fashion with an air space in between; and
   (c) an annular ridge of rigid material formed as an integral part of the cylindrical output section of said rigid connector and extending between the cylindrical output section and the cylindrical wall surface of said resilient, hollow tube, said annular ridge having a rounded tip physically engaging and depressing the cylindrical surface of said resilient hollow tube thereby forming an airtight seal between the cylindrical output section of said rigid connector and said resilient hollow tube; the tip of said annular ridge having a low coefficient of friction for providing a bearing-like surface against the depressed cylindrical surface of said resilient, hollow tube to permit said rigid connector to be rotated about the axis of said bore relative to said resilient, hollow tube in a swivel-like manner while maintaining said airtight seal.

15. The swivel coupling between a hollow cylindrical tube and a rigid, nonperforated hollow connector as defined by claim 14 wherein said hollow tube of resilient material is an endotracheal tube having an open proximal end and wherein the input section of said connector of rigid, nonperforated material is adapted for coupling said connector to the output breathing circuit connection of an anesthesiology machine.

* * * * *